United States Patent [19]
Khaw et al.

[11] Patent Number: 5,780,052
[45] Date of Patent: Jul. 14, 1998

[54] COMPOSITIONS AND METHODS USEFUL FOR INHIBITING CELL DEATH AND FOR DELIVERING AN AGENT INTO A CELL

[75] Inventors: Ban An Khaw, Milton; Vladmir P. Torchilin, Charlestown; Jagat Narula; Imran Vural, both of Brookline, all of Mass.

[73] Assignee: Northeastern University, Boston, Mass.

[21] Appl. No.: 427,676

[22] Filed: Apr. 24, 1995

[51] Int. Cl.$^6$ .................................................... A61K 9/127
[52] U.S. Cl. ............................................ 424/450; 436/829
[58] Field of Search ............................ 424/450; 436/829

[56] References Cited

U.S. PATENT DOCUMENTS 4,957,735   9/1990   Huang ................................... 424/85.8
5,230,900   7/1993   Hakamori ............................... 424/450

OTHER PUBLICATIONS

Machy et al., "Gene transfer from targeted liposomes to specific lymphoid cells by electroporation," *Proc. Natl. Acad. Sci. USA* 85:8027–8031 (1988).

Mueller et al., "Liposome Concentration in Canine Ischemic Myocardium and Depolarized Myocardial Cells," *Circulation Research* 49:405–415 (1981).

Khaw et al., "Monoclonal Antibody to Cardiac Myosin: Imaging of Experimental Myocardial Infarction," *Hybridoma* 3:11–23 (1984).

Torchilin et al., "Targeted accumulation of polyethylene glycol–coated immunoliposomes in infarcted rabbit myocardium," *The FASEB Journal* 6:2716–2719 (1992).

Torchilin et al., "Preservation of antimyosin activity after covalent coupling to liposomes," *Biochemical & Biophysical Research Communications* 89:1114 (1979).

*Primary Examiner*—Gollamudi S. Kishore
*Attorney, Agent, or Firm*—Weingarten, Schurgin, Gagnebin & Hayes LLP

[57] ABSTRACT

The invention relates to methods of salvaging a target cell from cell death, comprising contacting a target cell having a disrupted cell membrane with a specific affinity reagent-liposome conjugate in an amount effective and for a time sufficient to allow the conjugate to prevent cell death due to membrane disruption; and determining the viability of the target cell. Methods of delivering a selected agent into a damaged target cell for diagnosis and therapy are also disclosed.

3 Claims, 8 Drawing Sheets
(9 of 12 Drawing(s) in Color)

COMPOSITIONS AND METHODS USEFUL FOR INHIBITING CELL DEATH AND FOR DELIVERING AN AGENT INTO A CELL

FIELD OF THE INVENTION

The invention relates to compositions and methods use inhibiting cell death and for delivering an agent into a cell.

BACKGROUND OF THE INVENTION

Proteins and phospholipids are the most abundant constituents of cellular membranes, a phospholipid molecule having a polar head group and two nonpolar, hydrophobic fatty acyl chains. Phospholipids can exist in different forms in aqueous solutions, among which are spherical phospholipid bilayer structures or liposomes, which have an aqueous interior.

Liposomes have been shown to be useful as drug delivery vehicles. A number of reviews have described studies of liposome production methodology and properties, their use as carriers for drugs and their interaction with a variety of cell types. See, for example, "Liposomes as Drug Carriers," Wiley and Sons, N.Y. (1988), and "Liposomes from Biophysics to Therapeutics," Marcel Dekker, N.Y. (1987).

Delivery of drugs using liposomes allows for noninvasive treatment of diseases. Targeting of an organ or tissue type may be made more efficient using immunoliposomes, i.e., liposomes which are conjugated to an antibody specific for an organ-specific or tissue-specific antigen. Thus, one approach to targeted drug delivery is the use of drug-laden liposomes that have been made target-specific by incorporation of specific antibodies on the liposome surface. Such a system has been described using antimyosin antibody for targeting of liposomes to infarcted myocardium (Torchilin et al., Biochem. Biophys. Res. Comm. 89:1114, 1979, hereby incorporated by reference). Normal myocardial cells with intact cell membranes do not permit extracellular macromolecules, such as antimyosin antibody, to traverse the cell membrane and interact with the intracellular constituents. However, necrotic myocytes with membrane disruptions can no longer keep antimyosin antibody from interacting with intracellular myosin exposed to the exterior through cell membrane breaches (Khaw et al., Hybridoma 3:11–23, 1984). Immunoliposome-associated reagents have been reported to result in less than optimal accumulation at target sites, possible due to sequestration by the reticuloendothelial system, primarily by the liver and spleen. Torchilin et al. (FASEB Journal 6:2716, 1992) report on enhancement of circulation times using polyethylene glycol-coated immunoliposomes.

SUMMARY OF THE INVENTION

The invention is based on the discovery that specific affinity reagent-liposome conjugates may be contacted with cells that are in the process of dying so as to inhibit cell death. The invention encompasses two aspects, i.e., inhibition of cell death via cell membrane sealing, and delivery of an agent to a cell via cell membrane sealing. Both aspects of the invention utilize specific affinity reagent-liposome conjugates.

Thus, one aspect of the invention is directed to a method of salvaging a target cell from cell death, comprising contacting a target cell having a disrupted cell membrane with a specific affinity reagent-liposome conjugate in an amount effective and for a time sufficient to allow the conjugate to prevent cell death due to membrane disruption; and determining the viability of the target cell.

This aspect of the invention also involves contacting a specific affinity reagent-liposome conjugate, in which the specific affinity reagent portion recognizes and binds to an intracellular antigen, with a target cell having a disrupted cell membrane so as to allow the specific affinity reagent portion to adhere to the intracellular antigen, the adherence resulting in initially plugging the lesions in the membrane followed by sealing of the cell membrane and inhibiting or arresting the process of necrosis or cell death.

In a second aspect, the invention is directed to contacting a specific affinity reagent-liposome conjugate with a target cell to which an agent is to be delivered, the agent being carried in the liposome portion of the conjugate, where contact of the conjugate with the target cell results in delivery of the agent to the cell, followed by cell membrane healing as described above. Preferably, the conjugate includes a biological agent or a nucleic acid.

Thus, the second aspect involves a method of delivering a liposome-encapsulated biological agent or nucleic acid to a tissue containing both healthy cells and membrane-disrupted cells, the membrane disruption either existing naturally or having been induced specifically. The method includes contacting the tissue with an effective amount of a specific affinity reagent-liposome conjugate containing the biological agent or nucleic acid and targeted to membrane-disrupted cells of the tissue. Contact of the conjugate with the target cells results in delivery of the agent to the cells of the tissue and restoration of the integrity of the cell membrane.

In preferred embodiments of both aspects of the invention, the specific affinity reagent comprises an antibody, and the antibody may be specific for and bind to an intracellular antigen such as a cytoskeletal antigen. The tissue may comprise cardiac tissue, and the antibody may thus be specific for an intracellular antigen of cardiac tissue. The tissue may be cancerous or normal.

The invention also features methods of inhibiting cell death in cardiac tissue, comprising providing cardiac tissue containing cardiomyocytes having intracellular myosin exposed at the cell exterior; contacting the cardiomyocytes with a conjugate comprising an immunoliposome comprising an antibody specific for an intracellular antigen of cardiomyocytes for a time sufficient to allow the conjugate to adhere to the cardiomyocyte; and determining the viability of cells of the tissue. Preferably, the intracellular antigen comprises myosin.

The invention also features a method of delivering genetic material to a cell, comprising contacting a specific affinity reagent-liposome conjugate containing genetic material with a cell having a disrupted cell membrane for a time and in an amount sufficient to deliver genetic material to the cell and to prevent death of the cell; and determining the viability of the cell.

The invention also encompasses a method for enhancing in a mammal the effects of therapy that kills malignant cells in vivo, comprising the steps of: providing an immunoliposome specific for an internal cellular antigen present in degenerating neoplastic cells that is not present on the exterior of such cells, wherein the immunoliposome contains an antineoplastic agent; initiating therapy in a mammal to kill malignant cells in vivo, thereby causing some of the malignant cells to become necrotic; and administering the immunoliposomes to the mammal whereby the antibodies become bound to the internal cellular antigen present in necrotic malignant cells, thereby delivering the antineoplastic agent into the cells.

Preferably, the antineoplastic agent is selected from the group consisting of cytotoxic agents, toxins, radiosensitizing compounds, alpha-emitting radionuclides, beta-emitting radionuclides, antiproliferative agents and genes (for cytokines such as IL-2 and TNF). Preferably, the cells are killed with radiation, chemotherapy or immunotherapy.

As used herein, "specific affinity reagent" refers to any organic substance which has affinity for (i.e., binds to a substantially greater degree to) the target substance or molecule than for a non-target substance or molecule. As used herein, the term includes antibodies specific for certain organs, tissues, cells, or cellular antigens, particularly intracellular antigens, and also includes ligands for which an internal cellular receptor exists.

In preferred embodiments of both aspects of the invention, the specific affinity reagent may be an antibody, e.g., specific for an intracellular antigen, or a ligand that binds to an intracellular receptor. "Intracellular antigen" is meant to include antigens present in both neoplastic and normal cells, but not to antigens released into the general circulation upon cell death or to antigen on the exterior of living cells. "Tissue" refers to an agglomeration of cells that live in contact with each other in vivo, and may refer to both normal and abnormal tissues, including tumors, cancers, precancers, and neoplasms.

A "disrupted cell membrane" is defined herein as a cell membrane containing a physical disruption, e.g., a lesion, breach or hole through which the intracellular contents are accessible from the exterior of the cell. "Healthy" cells do not normally have disrupted cell membranes and their intracellular contents are not normally accessible from the external cellular environment; therefore, an "unhealthy" cell refers to a cell having a disrupted cell membrane, i.e., a cell that is in the early stages of the process of cell death.

As used herein, "necrosis" refers to the process that cells undergo as they die and involves a physical disruption of the cell membrane. Upon initiation of necrosis, the integrity of the cell membrane is lost as the membrane is dissolved to form a lesion. At the site of lesion, the cell membrane is gradually destroyed by biological, enzymatic and chemical degradation. At later stages of necrosis, more intracellular components, including nuclear antigens, structural elements in the cell, and organelles, eventually wash out, leaving a cell ghost, i.e., insoluble structural components of the cell and cell membrane. As used herein, cell death by necrosis is inhibited, prevented, or reversed upon sealing of a disrupted cell membrane by immunoliposomes.

A "salvageable" membrane-disrupted cell is a cell which can be contacted with immunoliposomes so as to reverse the dying process. Thus, "salvageable" cells refers to those cells which are in an early stage of necrosis, i.e., which possess some lesions or holes in the cell membrane, rendering one or more intracellular antigens accessible from the cell's exterior, but which still retain the cell nucleus and organelles. A salvageable cell will contain an intact nucleus and will not expose internal nuclear antigens to the cell exterior.

An "unsalvageable" cell is a membrane disrupted cell that has progressed beyond the stage of early necrosis, i.e., which has developed large membrane lesions and has lost structural elements in the cell such as cell organelles, and which may retain a cell ghost. An unsalvageable cell will expose internal nuclear antigens to the cell's exterior, and may have lost the nucleus altogether, and thus cannot be prevented from dying upon exposure to immunoliposomes.

A "healthy" cell includes cells that are not membrane-disrupted and thus their intracellular antigens are not exposed to the extracellular environment. Thus, contacting of a healthy cell with an immunoliposome specific for an intracellular antigen will not result in binding of the antibody portion of the liposome to that antigen.

An "unhealthy" cell refers to cells that contain a breach or disruption in the cell membrane severe enough to expose an intracellular antigen to the extracellular environment. Thus, contacting of an unhealthy cell with an immunoliposome specific for an intracellular antigen will result in binding of the antibody portion of the liposome to the intracellular antigen. "Delivery" of a biological agent or nucleic acid into a cell may be determined by direct or indirect methods, depending upon the substance delivered. For example, where a nucleic acid is delivered, viable cells may be assessed for the presence or absence of the nucleic acid (e.g., via hybridization) or for gene expression and detection of the expressed product.

A biological "drug" or "agent" includes both therapeutic agents and effector molecules. A "therapeutic agent" refers to, e.g., antineoplastic agents and other pharmaceuticals and genes (for tissue transformation or differentiation). An "effector molecule" refers to, e.g., cytotoxic molecules, radionuclides, imaging agents, reporter groups, etiologic agents of infectious diseases, metal chelating agents for radionuclide or paramagnetic metal ions, and genes (e.g., IL-2, TNF) which can mobilize the immune effector cells.

An "effective amount" refers to an amount sufficient to result in the desired effect at the target site; for example, where membrane sealing of a disrupted membrane is desired, an amount of immunoliposome sufficient to arrive at the target membrane lesion and inhibit cell death will be considered an effective amount. Alternatively, where a drug or gene is desired to be delivered to a target cell, tissue or organ, an amount of the drug or gene is loaded into an immunoliposome and an amount of loaded immunoliposome is delivered to the target site, the amounts in combination being sufficient to observe the desired effect upon delivery of the drug or gene to the site.

Therapeutic uses of the methods of the invention include therapeutic intervention after thrombolytic drug treatment, enhanced delivery of genetic material as for gene therapy, and improved delivery of drugs for cancer therapy.

Further features will become more fully apparent in the following description of the embodiments of this invention and from the appended claims.

DETAILED DESCRIPTION OF THE INVENTION

The invention is based on the discovery that immunoliposomes which are specific for a cellular antigen may be used for cell-targeting for the purpose of delivering a substance into the target cell or for inhibiting or reversing the process by which cells undergo death.

Cell Death

Necrosis and apoptosis are processes by which cells degenerate and eventually die. Cell death in an organ of the body may be the result of ischemic, inflammatory, immunologic and/or toxic insult to the tissue. Depending upon the location and severity of cell death, the consequences may be benign or significant enough to result in severe illness or death. Necrosis involves a physical disruption of the cell membrane due to oxygen deprivation or other chemical means. Upon initiation of necrosis, the integrity of the cell membrane is lost as the membrane is dissolved to form a lesion. At the site of lesion, the cell membrane may be gradually destroyed by phagocytosis and enzymatic degradation, and intracellular components, including nuclear antigens, structural elements in the cell, and organelles, eventually wash out.

Reperfusion injury is also believed to result in significant cell death. When blood is restored to a vascular area during reperfusion, oxygen is returned to an oxygen-deprived area and superoxide radicals may form, causing damage to cell membranes.

Cell death or viability may be determined according to the invention by one of several different methods. Dead cells can be distinguished from viable, i.e., live cells via conventional trypan blue exclusion, with dead cells appearing blue (e.g., using reagents as described in the catalogue of Sigma Chemical Co., 1995, p. 1681). In addition, cell death is determined by culturing cells in a culture dish or flask, wherein dead cells will float freely in the medium and live cells will adhere to the walls of the flask, as taught herein. Alternatively, cell viability may be determined via $^3$H-thymidine uptake by standard methods well known to those of ordinary skill in the art.

Liposomes

Liposomes are composed of a bilayer lipid matrix that wraps around an aqueous volume, thus isolating it from the external medium. The central aqueous core may vary in diameter from 20 nm to as much as 2–3 micrometers. The term "liposome", as used herein, is also intended to encompass liposomes which are composed of several (e.g., 2–3) concentric bilayers which define several individual aqueous compartments. Thermodynamically, liposomes have minimum free energy as long as the density of the phospholipids in each monolayer of the bilayer structure is the same.

Liposomes useful in the invention are composed of phospholipid molecules. A phospholipid molecule has a polar head group and two nonpolar, hydrophobic fatty acyl chains. In an aqueous environment, the most energetically stable form for phospholipids is within structures that allow the fatty acyl chains to avoid contact with water. A lipid bilayer is one such structure. Many phospholipids, when dispersed in water, spontaneously form lipid bilayer structures. Lipid bilayer structures useful in the invention are preferably circular structures.

The polar head group of the phospholipid molecule may include choline, e.g., lecithins (phosphatidylcholines) and sphingomyelins. Such molecules may also include amino groups, e.g., phosphatidylserine and phosphatidyl ethanolamine. Other polar head groups may include phosphatidylglycerol, phosphatidylinositol and cardiolipin.

The invention contemplates the use of immunoliposomes to inhibit or reverse cell death, or for delivering an agent to a target cell. An immunoliposome will include a liposome component, as described above, conjugated via its polar head group to the carboxy terminus of an immunoglobulin molecule. Fusion of an immunoliposome with the cell membrane will occur because most cell membranes are composed of protein and phospholipid bilayers. Immunoglobulins will be used for targeting liposomes to dying cells.

Mechanism of Action

Figure 1:
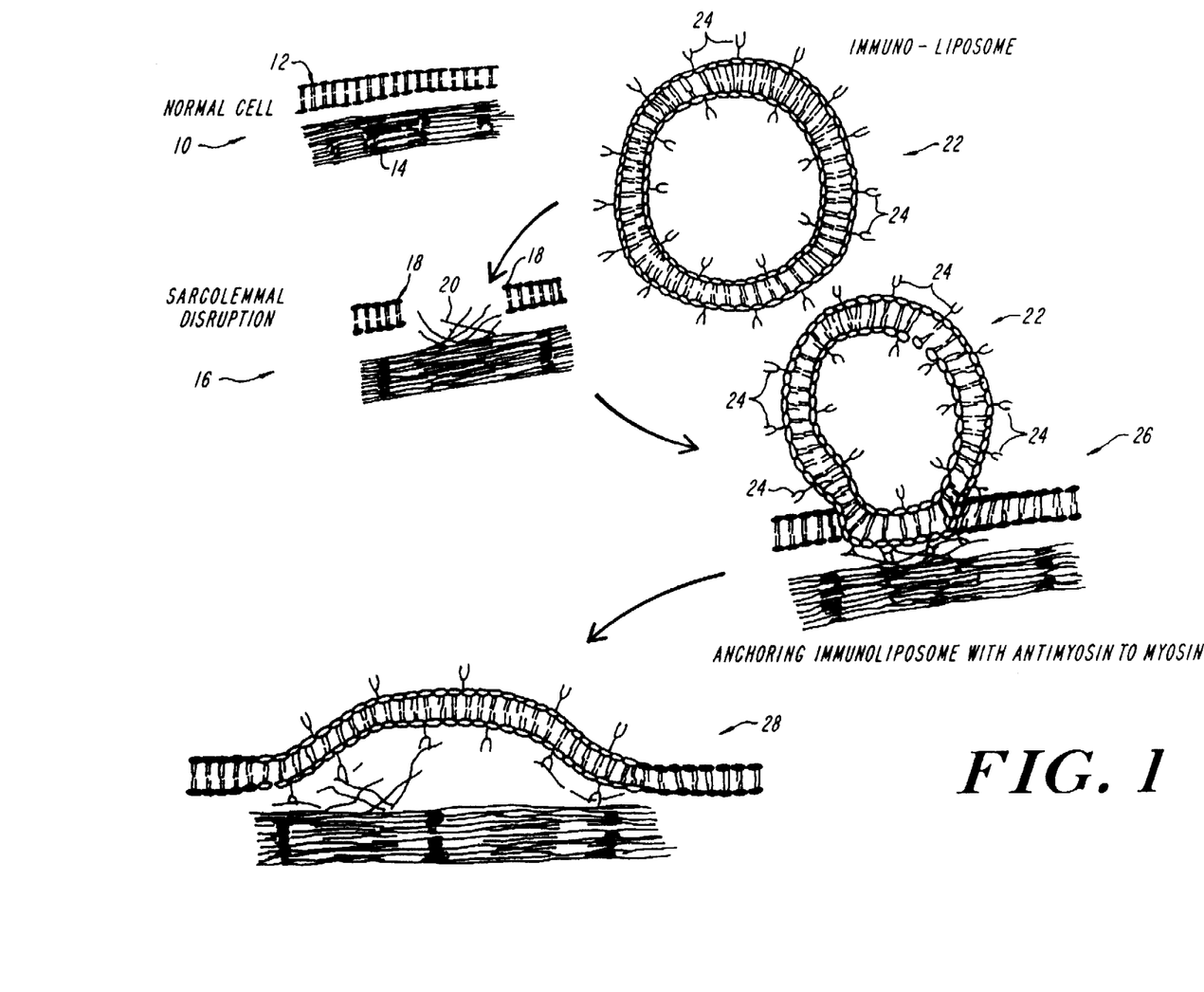
FIG. 1 is a schematic representation of the proposed mechanism of sarcolemmal repair.

Without being bound to any one theory, it is hypothesized that cell death in membrane-disrupted cells is inhibited or reversed as a result of immunoliposome-induced sealing of the cell membrane at the site of disruption. FIG. 1 is a schematic representation of the proposed mechanism of sarcolemmal repair. In FIG. 1, a portion 10 of a normal cardiac cell is shown, in which the cell membrane lipid bilayer 12 is intact and overlies myosin 14. FIG. 1 also depicts a disrupted cell membrane 16 in which the lipid bilayer 18 is breached and myosin strands 20 are exposed. The hypothesis contemplates specific targeting of an immunoliposome to the site of breach 18, the specificity being conferred via antibody/antigen interaction. That is, immunoliposomes 22 containing antibodies specific for myosin (anti-myosin antibodies 24) specifically target and bind to the exposed myosin in the region of breach, thus anchoring the immunoliposome to the disrupted cell at the site of breach 26. Such anchoring is believed to inhibit cell death by effectively plugging the membrane lesion, thus preventing the continued process leading to cell death, e.g., the intracellular contents from washing out. Fusion 28 of the immunoliposome to the disrupted cell membrane may follow anchoring, thus allowing interaction between anti-myosin antibodies and myosin over a greater area of the cell, and initiate repair of the membrane breach. Irrespective of the exact mechanism involved, the intraliposomal contents can also be delivered ultimately into the intracellular space. Therefore, the method of the invention is amenable as a general delivery technique, e.g., for a biological agent or nucleic acid.

Preparation of Liposomes and Immunoliposomes

Liposomes and immunoliposomes may be prepared according to a variety of techniques, e.g., detergent dialysis or the formation of a water-in-oil emulsion, slow swelling in nonelectrolytes, dehydration followed by rehydration, dilution or dialysis of lipids in the presence of chaotropic ions, and mechanical preparation techniques such as freeze-thaw cycling.

Removal of detergent molecules from aqueous dispersions of phospholipid/detergent mixed micelles represents one way of producing liposomes (see J. Biol Chem. 246:5477 (1971) herein incorporated by reference). As the detergent is removed, the micelles become progressively richer in phospholipid and finally coalesce to form closed, single bilayer vesicles. Detergents commonly used for this purpose include bile salts and octylglycoside. Because this method does not involve the use of organic solvents and sonication, it is particularly useful for entrapping macromolecules, such as proteins and nucleic acids, which are sensitive to the presence of organic solvents or are structurally altered by sonication.

Another method of preparing liposomes is the reverse phase evaporation method detailed in U.S. Pat. No. 4,235,871, which is incorporated herein by reference. Liposomes prepared by this method have a typical average size of about 2–4 microns and are predominantly oligolamellar, that is, contain one or a few lipid bilayer shells.

Liposomes may also be prepared via hydration in the presence of a solvent. Multi-lamellar vesicles (MLVs) with high encapsulation efficiency can be prepared by hydrating the lipids in the presence of an organic solvent. The two phases are emulsified by vigorous mixing (vortexing) and then the organic phase removed by passing a stream of nitrogen gas over the emulsion. As the solvent evaporates, liposomes form in the aqueous phase.

Mechanical preparation methods, e.g., shaking by hand, sonication, French pressure freeze-drying, membrane extrusion, freeze-thawing, changing pH, calcium inducing, and micro emulsion techniques, have been used for the preparation of liposomes. In essence, a mixture of vesicle-forming lipids in a volatile organic solvent is deposited on the surface of a round bottomed flask, and the solvent is removed by rotary evaporation under reduced pressure. Vesicles ranging in size from one-tenth to tens of microns form spontaneously when an excess volume of aqueous buffer is added with agitation to the dry lipid. The drug to be entrapped may be included either in the lipid film (for a lipophilic drug) or in the aqueous hydration medium (for a hydrophilic drug).

Methods for controlling the size of liposomes are various and include extrusion and homogenization. One effective sizing method involves extruding an aqueous suspension of the liposomes through a series of polycarbonate membranes having a selected uniform pore size in the range of 0.2–0.6 micron, typically 0.1–0.2 micron. The pore size of the membrane corresponds roughly to the largest sizes of liposomes produced by extrusion through that membrane, particularly where the preparation is extruded two or more times through the same membrane. Extrusion of liposomes can also be performed through an asymmetric ceramic filter, as taught in U.S. Pat. No. 4,737,323, herein incorporated by reference. Other methods of reducing particle size include application of high pressures to the liposomes, as in a French Press, and homogenization of the liposomes.

Immunoliposomes

Antibodies, and in particular monoclonal antibodies, are the focus of intense interest in the field of cancer research. Antibodies have been developed to cell-surface antigens for a number of malignancies, but are useful only in restricted categories of tumors. Techniques are known for conjugating such antibodies to pharmacologically active agents or to labels to permit diagnosis, localization, and therapy directed toward such tumors.

Recent research has led to the identification of unique nuclear antigens and development of monoclonal antibodies thereto. See, e.g., Epstein and Clevenger, Exp. Cell. Res. 151:194 (1984) and J. Histochem. and Cytochem. 32:757 (1984). Such antibodies have been labeled and used to identify structures in the nucleus.

Liposome targeting based on antibody/antigen recognition has been utilized in the prior art in the development of targeted delivery systems for delivery of various bioactive agents to a target site. Antibody-directed liposomes, or immunoliposomes, are used for this purpose. Antibody molecules are predominantly hydrophilic compounds with no affinity for the hydrophobic liposome membrane.

As used herein, an immunoliposome comprises a liposome conjugated to an immunoglobulin molecule. Generally and as used herein, a liposome/immunoglobulin conjugate comprises an immunoglobulin molecule linked via direct or indirect means and either covalently or noncovalently to the phospholipid molecule. Generally, about 1 in every 200 phospholipid molecules of the liposome will be linked to an antibody molecule, with an acceptable range being 1 in every 20–20,000 phospholipid molecules of the liposome.

Where enhancement of specificity of the immunoliposome for the target site is desired, the immunoliposome may include antibodies of several different specificities, each cognate antigen being found at the target site. Such multiple specificity may also be conferred using bifunctional or trifunctional antibodies (see, e.g., U.S. Pat. No. 5,237,743, hereby incorporated by reference).

Methods are known in the prior art for preparing immunoliposomes. Immunoliposomes are prepared, for example, by adsorption of proteins (e.g., immunoglobulin) on the liposomal surface; incorporation of native protein into the liposome membrane during its formation (e.g., by ultrasonication, detergent dialysis or reverse phase evaporation); covalent binding (direct or via a spacer group) of a protein to reactive compounds incorporated into the liposomes membrane; noncovalent hydrophobic binding of modified proteins during liposome formation or by the incubation with preformed liposomes); and indirect binding, including covalent binding of immunoglobulin protein via a polymer to the liposome (see Torchilin, V. P. CRC Critical reviews in Therapeutic Drug Carrier Systems, vol. 2(1), hereby incorporated by reference).

Immunoliposomes may be prepared according to the following procedure.

1. Covalent Coupling of Antibody with NGPE.

0.6 mg N-Glutaryl phosphatidylethanolamine (NGPE) was dissolved in 0.5 cc 2-[N-morpholino]ethanesulfonic acid hemisodium salt (MES) buffer (in 0.016M octylglucoside in 50 mM MES). After the addition of 4.8 mg 1-ethyl-3-(3-dimethylaminopropyl)carbodiimide (EDC) and 6 mg N-hydroxysulfosuccinimide (HSSI), the resulting mixture was incubated at room temperature for 5 min. The antibody solution (containing antimyosin antibody 2G42D7, described below, or other antibody) was then added (0.36 mg/ml). The pH of the mixture was then adjusted to 8.0 with 1M NaOH. The reaction mixture was incubated at 4° C. for 8–12 hour with mixing. The resulting NGPE-antibody conjugate was then dialyzed overnight against PBS, pH 7.4 to remove octylglucoside and other excess reagents.

2. Preparation of Immunoliposomes by detergent dialysis.

Liposomes were prepared from a mixture of egg phosphatidylcholine (PC) and cholesterol (Ch) in chloroform in the molar ratio 1:1. The lipid mixture (30 mg PC/17.96 mg Ch) was dried with argon, then vacuum dried for 2 hour and resuspended in 4 cc phosphate buffered saline (PBS) containing 0.016M octylglucoside with brief ultrasonication. The solution of NGPE-modified antibody (0.7 mg/ml) was added to solubilized lipids. The mixture was dialyzed overnight against PBS (pH 7.4) to remove detergent. The resulting liposomes were extruded through a Nucleopore filter (0.6, 0.4, and 0.2 μm). The same method was used for preparation of liposomes without NGPE-antibody solution.

3. Preparation of Fluorescent Liposomes.

Liposomes were prepared from a mixture of egg phosphatidylcholine (PC), cholesterol (Ch) and L-α phosphatidylethanolamine-N-fluorescein (FL) in chloroform. The lipid mixture (30 mg PC/17.96 mg CH/0.1 mg FL) were dried with argon, then vacuum dried for 2 hour and resuspended in 4 cc PBS containing 0.016M octylglucoside with brief ultrasonication. The solution of NGPE-modified antibody (0.7 mg/ml) was added to the solubilized lipid. The mixture was dialyzed overnight against PBS (pH 7.4) to remove detergent. The resulting liposomes were extruded through a Nucleopore filter (0.6, 0.4, and 0.2 μm). The same method was used for liposomes without NGPE-antibody solution.

4. Preparation of electron-dense Antimyosin Immunoliposomes.

For ultrastructural characterization of antimyosin liposome sealing, electron-dense antimyosin immunoliposomes were prepared. Lipid mixture (30 mg PC/17.96 mg Ch) was dried with argon then vacuum dried for 2 hour and resuspended in NGPE-antibody solution (0.7 mg/ml). Two mg $AgNO_3$ was added to the solution, which was vortexed and sonicated slightly. The resulting liposomes were extruded through filter (0. 6, 0.4, 0.2 μm). The mixture was dialyzed overnight against water. 200 μl 0.145M NaCl was added and the mixture was exposed to light for 1 hour. For processing of electron microscopic characterization, liposome containing medium was removed, cells were washed with PBS (pH 7.4). The cells were then fixed with 2.5% glutaraldehyde plus 2% paraformaldehyde in 0.1M Na cacodylate buffer pH 7.2. Fixed and pelleted cells were dehydrated in an alcohol series. Ultrathin sections contrasted with uranyl acetate and lead citrate was studied in transmission electron microscopy (TEM).

Loading of Immunoliposomes

Loading of compounds into liposomes may be achieved by one or more of a variety of active and passive methods. Passive loading by entrapment is employed for those compounds which are therapeutically active at relatively low drug doses, for drugs which are highly soluble in aqueous solutions, or for DNA which is expressed at a high efficiency in a target cell. It has been found that for certain hydrophobic drugs, that the highest concentration of encapsulated material which can be achieved by passive loading is limited by their low intrinsic water solubility. The concentration of hydrophobic drug that can be accommodated in the liposome will depend on drug/lipid interactions in the membrane, but is generally limited to a drug concentration of less than about 20 mcg drug/mg lipid. In the case of amphipathic drugs having a positive charge, it has been found that inclusion of 20–30 mole percent of an anionic phospholipid in the liposomal membrane results in increasing the loading factor significantly through formation of an "ion pair" complex with the negatively charged phospholipid at the membrane interface.

Loading of high concentrations of drugs in liposomes may require active loading methods, e.g., as described in U.S. Pat. No. 5,129,549, herein incorporated by reference, in which a chemical gradient is created across the liposome membrane that results in trapping of the drug in the internal aqueous phase of the liposome.

Liposome/drug formulations are characterized by measurements of particle size, lipid concentration, and pH by standard methods as described above. Drug incorporation into the composition may be determined by inclusion of radiolabeled tracer in the composition. The amount of liposome-entrapped drug is then determined by gel permeation chromatography using BioRad A-15M resin. The liposomal drug fraction is calculated from the amount of radiolabel present in the void volume of the column, and the percentage of liposomal drug from the ratio of label eluting in the void volume to the remaining label eluting from the column.

Preparation of Antibodies

Immunoglobulin molecules useful in the invention include whole antibody, or any antibody fragment, for example, a F(ab')2, Fab, and/or an Fv fragment of an antibody molecule. In addition, any variable region specificity of an antibody molecule is useful according to the invention.

A F(ab')2 fragment is that portion of an antibody molecule which contains the complete antigen-combining site, consisting of two light chains and part of each heavy chain, and is produced by enzymatic digestion, e.g., using pepsin, such that the heavy chain disulfide bonds remain intact in the F(ab')2 fragment. A Fab fragment consists of a single light chain and a part of a heavy chain disulfide bonded together. Fab is produced by enzymatic digestion, e.g., using papain, such that about one-half the F(ab')2 antigen binding fragment is generated. An Fc fragment is that portion of an antibody that is responsible for binding to antibody receptors on cells and the Clq component of complement. The Fc fragment is the portion of the antibody molecule that remains after papain digestion. An Fv fragment is that portion of an antibody consisting of the variable region of a Fab fragment.

Antibodies useful in the invention may be obtained through conventional polyclonal or monoclonal antibody preparation techniques. Antigen may be obtained from cells of the species toward which the antibodies are to be directed. Such species are preferably vertebrate, more preferably mammalian, and most preferably human. For antibodies directed toward human intracellular antigens, immortal cell lines represent a convenient source of such antigen.

To generate monoclonal antibodies, murine spleen cells from immunized animals are fused with an appropriate myeloma cell line. Fused cells are cultured in selective growth medium to establish hybridoma colonies, each colony secreting an antibody of interest. Culture supernatants from each colony are then tested for antibody specificity. Positive cultures are identified and expanded. See Kohler et al., Nature 256:495 (1975), hereby incorporated by reference.

Target Antigens

Antigens useful in the invention include intracellular antigens, preferably cytoskeletal antigens, for specific cell types that are to undergo treatment. These cell types include any type of cell that is useful as a target for cell salvage or for gene therapy, including but not limited to cardiac muscle cells, skeletal muscle cells, liver cells, and spleen cells. The antigens include intracellular antigens, and antigens which are more available for binding when a cell, tissue, or organ is in a diseased or unhealthy state than in a healthy state. Intracellular cytoskeletal antigens will be particularly useful for anchoring of the immunoliposomes used to plug a membrane lesion.

Antibodies that are useful for targeting such antigens include but are not limited to: anti-myosin antibody (for example, R11D10, Centocor, Malvern, Pa. or 2642D7 (described below)), anti-actin antibody, anti-cytoskeletal antibodies, anti-histone antibody, anti-nuclear antibodies, anti-endoplasmic reticulum antibody, and anti-protein kinase C antibody. All such antibodies are publicly available through the American Type Culture Collection, 12301 Parklawn Drive, Rockville, Md. 20852, U.S.A.

In order to screen for monoclonal antibodies that bind specifically to cells undergoing the process of cell death, i.e., that bind to intracellular antigens, equal aliquots are prepared from cell cultures, one aliquot containing healthy cells and another aliquot containing cells that have been subject to several cycles of vigorous pipetting to disrupt cell membranes. Cells having undergone membrane disruption will uncover intracellular components for antibody recognition that would not normally be available for such recognition in the absence of membrane lesions. The ability of a monoclonal antibody from each test aliquot to bind the healthy or membrane disrupted cells is then quantitatively measured, e.g., by radioimmunoassay or direct or indirect immunofluorescence screening techniques. Specificity for intracellular antigens is determined by comparing binding to the test aliquots. Those antibodies which bind only to the membrane disrupted cells, and do not bind to healthy cells, can be considered good candidates for possessing specificity to intracellular antigens.

Because even a healthy cell culture may contain a relatively large proportion of necrotic cells, an antibody that is specific for an intracellular antigen may exhibit some binding to the healthy cell culture. It should also be recognized that even though the antibody may not be specific to any surface protein or antigen of the cell line employed in the screening process, certain tumor cell lines (such as histiocytic cell lines) have surface components that exhibit generalized binding of immunoglobulins.

Therefore, it is preferable to perform a second screening step for antibodies to intracellular antigens, as identified above, the second step being to screen the candidate antibodies for comparative binding to similar in vivo cells that are healthy versus the same in vivo cells that have been cell membrane disrupted.

Labeling and Labels Useful in the Invention

The various labels listed below need not be limited to labeling of antibodies. Instead of antibodies, other carriers (synthetic or natural) may be used as recipients of the labels.

(1) Radiolabels

For imaging purposes, any of the well-known medical radionuclides can be used. Suitable radionuclides include Tc-99 m, I-123, I-125, In-111, In-113 m, Ga-67, or other suitable gamma-emitters.

For example, iodination, may be accomplished using the chloramine-T method described in Mills et al., Hybridoma 5: 265–275 (1986). This technique may be used to effect iodination to render the antibody radiopaque or to attach a radionuclide, such as I-125 or I-131.

Other radionuclides may be attached to the antibodies in question through chelation with benzyl EDTA or DPTA conjugation procedures. Still other suitable techniques include the iodogen method disclosed in Pimm et al., Int. J. Cancer 30:75 (1982), and direct iodination with radioactive sodium iodide.

(2) Radiopaque Materials

Radiopaque materials also may be used to label the antibodies. Suitable radiopaque materials are well known and include iodine compounds, barium compounds, gallium compounds, thallium compounds, and the like. Specific examples of radiopaque materials include barium, diatrizoate, ethiodized oil, gallium citrate, iocarmic acid, iocetamic acid, iodamide, iodipamide, iodoxamic acid, iogulamide, iohexol, iopamidol, iopanoic acid, iotasul, iotetric acid, iothalamic acid, iotroxic acid, ioxaglic acid, ioxotrizoic acid, ipodate, meglumine, metrizamide, metrizoate, propyliodone, and thallous chloride.

(3) Magnetic Resonance-Enhancing Materials

Materials that can be detected by or that enhance the effects of magnetic resonance imaging equipment also may be conjugated to the antibodies. Suitable conventional magnetic resonance-enhancing compounds include gadolinium, copper, iron, and chromium. It is preferred that these metal atoms be prepared in the form of a conventional organometallic chelates, which are then bound to the antibody.

Conjugation of Labels and Therapeutic Compounds to Antibodies or Other Carriers

Numerous techniques suitable for binding various molecules to antibodies or other carriers have been established. Numerous techniques are available for attaching various molecules, enzymes and proteins to antibodies. For example, many carboxylic acid-containing compounds (such as methotrexate) can be conjugated to immunoglobins through an active ester intermediate, formed, e.g., by reacting the compound with N-hydroxysuccinimide and dicyclohexylcarbodiimide. See, T. Deguchi, et al., Effect of Methotrexate-Monoclonal Anti-Prostatic Acid Phosphatase Antibody Conjugate on Human Prostate Tumor, Cancer Res. 46:3751–3755 (1986). Others, such as chlorambucil, will bind directly to the antibodies at low pH. See, e.g. T. Ghose, et al., Immunochemotherapy of Human Malignant Melanoma with Chloroambucil-Carryine Antibody. Europ. J. Cancer 11:321–326 (1975).

Amino sugar-containing drugs such as adriamycin and daunomycin may be covalently bound to antibodies by periodate oxidation of the drug, followed by linking of the oxidized drug to the immunoglobulin and subsequent reduction of the product with sodium borohydride. E. Hurwitz, et al., The Covalent Binding of Daunomycin and Adriamycin to Antibodies, Cancer Res. 35:1175–1181 (1975).

Conventional techniques also exist for binding biologically active molecules or other proteins to antibodies. Free thiol groups may be introduced into the antibody by reacting antibody with N-succinimidyl-3-(2-pyridyldithio) propionate (SPOP) to introduce 2-pyridyl disulphide groups. The protein to be bound to the antibody is incubated with SPDP. Upon mixing the SPDP-modified protein with the antibody containing free thiol groups, the two materials become bound.

Other known techniques, such as the use of dextran T-10 spacers to increase the number of drug moieties linked to antibody molecules can be employed, as can mixed anhydride methods of drug conjugation. The compound 1-ethyl-3-(3-dimethylaminopropyl) carbodiimide hydrochloride (ECDI) may be used to bind amino-containing drugs to the carboxyl groups of antibodies. Alternatively, glutaraldehyde may be used for crosslinking between free amino groups of the antibody and amino groups in the compound to be conjugated thereto.

Inhibition or Reversal of Cell Death in Cardiac Cells

Cell death in an organ such as the heart may be highly detrimental due to the inability of certain cells of the heart, e.g., cardiomyocytes, to proliferate and thus replace themselves. Cardiomyocytes are highly differentiated cells which are not capable of division.

The cardiac protein myosin is well known. This protein is an intracellular muscle protein found inside cardiac cells, but not on the cell wall. Myosin-specific antibodies have been developed and have been labeled for in vivo imaging of heart tissue damaged by myocardial infarction. (See, Khaw et al., J. Clin. Invest. 58:439, 1976).

Cardiac necrosis may be inhibited or reversed by administering immunoliposomes specific for, e.g., cardiac myosin, to a patient in an amount and for a time sufficient to inhibit or reverse cell death. Immunoliposomes may be administered intravenously as a single dosage, intermittently for, e.g., 1–10 min., or continuously over a period of hours or days, as required. Administration of myosin-specific immunoliposomes may be especially useful, e.g. during reperfusion therapy to off-set the injury to tissue that occurs during such therapy. Therapeutic immunoliposomes may also be delivered by intracoronary infusion directly into the region at risk as a co-therapeutic regimen to angioplasty or thrombolysis.

Therapeutic Agents

Therapeutic agents which may be encapsulated and thus used according to the invention for delivery to a target cell are presented in Table I. Table I is a list of representative useful agents and is not meant to be exhaustive. Generally, any therapeutic agent that is encapsulatable in a liposome and is therapeutically effective when used for targeted delivery is encompassed by the inventive methods. Also, as presented in Table I, antimyosin immunoliposomes can particularly be used for targeting of drugs likely to be of benefit for ischemically compromised myocardium.

aminoglutethimide, anthramycin, asparaginase, azacitidine, azetepa, bisantrene, bleomycin, busulfan, cactinomycin, calusterone, caracemide, carboplatin, carmustine, carubicin, chlorambucil, cisplatin, cyclophosphamide, cytarabine, dacarbazine, dactinomycin, daunorubicin, dezaguanine, diaziquone, doxorubicin, epipropidine, etoposide, etoprine, floxuridine, fludarabine, fluorouracil, fluorocitabine, hydroxyurea, iproplatin, leuprolide acetate, lomustine, mechlorethamine, megestrol acetate, melengestrol acetate, mercaptopurine, methotrexate, metoprine, mitocromin, mitogillin, mitomycin, mitosper, mitoxantrone, mycophenolic acid, nocodazole, nogalamycin, oxisuran, peliomycin, pentamustine, porfiromycin, prednimustine, procarbazine hydrochloride, puromycin, pyrazofurin, riboprine, semustine, sparsomycin, spirogermanium, spiromustine, spiroplatin, streptozocin, talisomycin, tegafur, tenoposide, teroxirone, thiamiprine, thioguanine, tiazofurin, triciribine phosphate, triethylenemelamine, trimetrexate, uracil

TABLE I

| Drug | Disease treated or effect desired | Probable benefit rendered by liposomes |
| --- | --- | --- |
| Amphotericin B | Systemic fungal infections | Significantly greater efficiency |
| Doxorubicin | Cancer | Reduced cardiotoxicity, immunosuppression emesis, alopecia; enhanced efficacy |
| Cisplatin | Cancer | Reduced nephrotoxicity and emesis. New indications in leukemias, Not cross-resistant with cisplatin lymphkomas and liver metastases. |
| Vincristine | Cancer | Reduced neurotoxicity; enhanced efficacy |
| Muranyltripeptide | Cancer-immunomodulator | Only acceptable carrier; targets to macrophages |
| Gentamicin | Gram-negative pneumonia; other gram negative infections | Reduced nephrotoxicity; significantly improved efficacy |
| Streptomycin | Bovine brucellosis | Only cure |
| Indomethacin | Arthritis | Reduced gastric toxicity |
| Bovine somatotropin | Increased milk production | Infrequent dosing, e.g., once every two weeks |
| Epithelial growth factor | Aid in wound healing | Infrequent dosing |
| Piloarpine | Glaucoma | Reduced dosing, e.g., one drop per day |
| Tear components | Dry eye | Increased comfort; longer lasting |
| Indium-111 | Tumor-imaging | Preferential accumulation in tumor |
| Fibroblastic growth factor-β | Neovascularization in the infarcted myocardium | Likely to be of benefit in post infarction period |
| Angiogenic factors | Neovascularizaton in the infarcted myocardium | Likely to be of benefit in post infarction period |
| High energy substrates for the myocardium | Supplemental for depleted source of energy | Likely to be of benefit in post infarction period |
| Antioxidants, e.g., superoxide dismutase β-hydroxy anisole | For prevention of free radical injury | Likely to be of benefit in reperfusion of ischemic myocardium |
| Cytokines, e.g., EGF, IL-1, IL-6 | Stimulation of myocardial cell | Likely to be of benefit in ischemic myocardium |
| Contrast agents e.g., urogoaffin | For production of specific contrast agents | Likely to be of radiodiagnostic use for myocyte necrosis |

[The first part of Table I is drawn from: Ostro, M. J., Introduction. In Liposomes: From Biophysics to Therapeutics. Ed.: Ostro, M. J. Marcel Decker, Inc., New York, 1987.]
[The second part of Table I is drawn from research leading to the invention, as described herein.]

A large number of antineoplastic agents are known which can be loaded into immunoliposomes and used as contemplated in the present invention. In addition to the above-listed agents, antineoplastic agents may include folate inhibitors, pyrimidine analogs, purine analogs, alkylating agents, antibiotics, and radiosensitizing compounds. Specific examples of such antineoplastic agents include acivicin, aclarubicin, acodazole, adriamycin, ametantrone, mustard, uredepa, vinblastine, vincristine, vindesine, vinepidine, vinrosidine, vinzolidine, zinostatin and zorubicin.

In addition, alpha-emitting and beta-emitting radionuclides may be used. Such compounds include I-131, Yt-99, Cu-67, Au-198, Re-186, Re-188, P-32, and other cytotoxic radionuclides.

According to the invention, immunoliposomes also may be the carriers of biological response modifiers, including cytokines such as interleukin-2, vasodilators, any of the interferons, tumor necrosis factor, and the like.

Yet another category of compounds that may be transported by immunoliposomes according to the present invention are toxins such as ricin, tetanus, diphtheria, abrin, gelonin, mistletoe, and other materials capable of causing localized necrosis.

Immunoliposomes for Delivery of DNA to Membrane-damaged Cells

Immunoliposomes prepared according to the invention can be used for delivery of DNA to a target cell in two unique ways.

1. Shove and Seal delivery: Intracellular DNA delivery using immunoliposomes seeking intracellular targets followed by effective salvage of the cells.

Immunoliposomes containing DNA may be prepared so as to specifically target intracellular antigens in cells having damaged cell membranes. One immunoliposome/antibody conjugate exemplified herein is specific for the intracellular antigen myosin; however, the invention encompasses the use of immunoliposomes/antibody conjugates in which the antibody is specific for and thus targets any intracellular antigen, e.g., cytoskeletal or contractile proteins.

The net delivery of gene copies from the immunoliposome to the intracellular milieu will be significantly higher due to the abundance of the intracellular antigen concentration. Concomitant with intracellular gene delivery, liposomes effectively seal the breaches in the cell membrane, and thus maintain cell viability.

2. Local depot delivery: Immunoliposomes using intracellular targets of irreversibly injured cells as anchors for gene delivery to surrounding tissues.

DNA delivery also can be targeted to irreversibly damaged cells, i.e., cells that are beyond the stage where they can be salvaged via liposomes sealing. Immunoliposomes target an intracellular antigen of the irreversibly damaged cell and become anchored to the intracellular antigen. The DNA-loaded liposomes can then release the gene fragments around the anchor and free interstitial DNA fragments will be avidly adsorbed by various interstitial cells.

For example, DNA may be delivered to irreversibly damaged myocardium. If cells are targeted in acute myocardial infarction, surrounding cells which pick up DNA such as myoD and myogenin, as reported in Taylor, J. of NIH Research 6:57–61 (1994), may upon integration and expression of the foreign DNA develop as skeletal mycocytes, thus restoring contractile elements to the otherwise fibrous scar. Thus, the mode of DNA delivery according to the invention provides noninvasive and effective delivery to a partially damaged target tissue.

Both the "shove and cork delivery" and "local depot delivery" methods can also be applied to treatment of diseases such as cancer or cystic fibrosis by selecting appropriate DNA coding sequences for targeted delivery. For example, cytokines and/or growth factors may be delivered to cancer cells. Tumors contain many micronecrotic centers, i.e., areas of membrane-damaged cells. Immunoliposomes containing DNA encoding TNF or IL-2 may be targeted to cytoskeletal structures in tumor cells via micronecrotic centers in the tumor. Delivery of the genetic construct to the micronecrotic center would also initiate repair and sealing of the damaged cell membrane. The revived cell can then begin to produce the necessary cytokines in situ to initiate gene therapy. The local depot delivery approach may also be used to target DNA-containing immunoliposomes to tumor associated antigen for anchoring the immunotherapeutic liposomes. Thus, the above-described two modes of gene therapy, i.e., using immunoliposomes for delivery of DNA to damaged but salvageable cells or to damaged and unsalvageable cells, may initiate gene therapy for a variety of therapeutic applications, including cardiovascular applications, and to tumor gene therapy.

Chemotherapy using Loaded Immunoliposomes

Modern techniques for nonsurgical treatment of cancer include both clinical and experimental techniques involving chemotherapy, radiation therapy, a combination of chemotherapy and radiation therapy, and immunotherapy. In each instance, the object of the therapy is to kill the malignant cells. Antineoplastic agents presently or potentially useful in such therapy include cytotoxic drugs, biological response modifiers, radiosensitizing compounds, toxins, and radionuclides.

Loaded immunoliposomes also may be used in cancer chemotherapy by delivering a radioactive agent to micronecrotic areas of a target site, e.g., a tumor, using immunoliposomes containing a labeled agent prepared as disclosed herein, or by delivering an immunoliposome containing an antineoplastic agent to a target site.

Antineoplastic agents useful according to the invention include but are not limited to cytotoxic agent, toxin, biological response modifier, radiosensitizing compound, alpha-emitting radionuclide, beta-emitting radionuclide, antiproliferative agent.

Diagnostic Procedures Using Immunoliposomes

One diagnostic procedure of the present invention involves diagnosing sites of necrosis in an organ or tissue. This procedure utilizes immunoliposomes specific for intracellular antigens and containing a diagnostic agent, e.g., a detectable molecule such as an imaging agent. One example of such an agent is a gamma-emitting radionuclide of the type previously discussed. The radionuclide may be attached to a convenient carrier molecule, such as a chelating polymer. The radionuclide-containing immunoliposome is injected (preferably intravenously) into a patient suspected of containing an organ or tissue that is undergoing cell death; for example, a patient who has received chemotherapy, radiation therapy, or both. This procedure is preferably carried out at least one or two days after the initiation of the therapy, in order to permit resultant necrosis of the neoplastic tissue to advance to a sufficient point that reasonable numbers of necrotic cells are present. Between 30 minutes and 3 days following administration of the labeled antibody, an appropriate scintigraphic imaging technique is employed to image the label that is localized in necrotic tissue. Suitable imaging techniques include gamma cameras and SPECT (single photon emission computed tomography) techniques.

One alternative imaging technique is radiographic imaging. In this technique, immunoliposomes specific for intracellular antigen that has been labeled with a radiopaque material is injected a suitable time after initiation of chemotherapy or radiation therapy. After the antibody has localized at the areas of necrotic tissue, radiographic imaging is performed. Other suitable techniques include CAT (computed axial tomography) scans, fluoroscopy and conventional X-ray imaging.

Therapeutic Procedures Using Immunoliposomes

By loading immunoliposomes of the present invention with therapeutic, e.g., antineoplastic compounds, those therapeutic agents may be delivered directly to the neoplasm, with greatly reduced systemic effect. Two approaches may be employed; first, as augmentation therapy following use of an existing therapeutic modality that may have killed all or part of the tumor; and second, as a primary de novo mode of therapy focusing on the neoplastic cells already showing some degree of abnormal permeability.

In the augmentation approach, tumor necrosis is initiated by any conventional technique, such as chemotherapy, immunotherapy, radiation therapy, or the like.

After initiation of such therapy, necrosis begins in the tumor mass. At this point (usually at least two days after initiation of the primary therapy), immunoliposomes containing the therapeutic compound, preferably an antineoplastic agent, are administered to the patient. Intravenous administration is preferred, although direct injection in the vicinity of the tumor is also contemplated.

Following administration of the loaded immunoliposomes, the immunoliposomes become bound to necrotic areas in the tumor mass, and deliver the antineoplastic agent to disrupted cells.

If a lethal amount of antineoplastic agent is delivered to a necrotic area, healthy, viable tumor cells surrounding this area may be rendered necrotic, enabling additional amounts of antineoplastic agent to penetrate the newly necrotic area. In this way, a diffusion effect may be possible with destruction of the tumor cells proceeding radially from necrotic to healthy tumor tissue. To achieve this diffusion effect, a cytotoxic agent such as a beta-emitting or an alpha-emitting radionuclide may be used.

In the second approach (primary therapy), the method is exactly as described above, except that the need for prior treatment with some other modality (to create an initial population of necrotic cells) is obviated.

The amount of antineoplastic agent-loaded immunoliposome administered to the patient will vary depending on the antineoplastic agent used and the size of the tumor. However, in general, the dosage is selected to administer a total dose of antineoplastic agent that is equal to or less than the conventional therapeutic dosage of the particular agent selected. It is preferred that the total dosage be between 1% and 50% of the conventional therapeutic dosage, and it is most preferred that the dosage be between 2% and 25% of the conventional therapeutic dosage of the compound. However, as with all cancer therapy, the optimum dosage will be determined by the treating physician based on the individual patient's response to the therapy and the side effects resulting therefrom.

Immunoliposomes are Efficient Sealers of Cell Membrane Lesions

Immunoliposomes are efficient sealers of cell membrane lesions, and thus are useful to protect membrane-damaged cells from further injury and death. Experimental evidence of efficient sealing by immunoliposomes of membrane-damaged cells is as follows. The examples provided herein utilize cardiac cells in a model system which mimics damage to cardiac cells as may occur in heart diseases.

H9C2 cardiomyocytes from the American Type Culture Collection (ATCC) in culture were subjected to hypoxic injury. Hypoxic myocytes were then incubated with one of antimyosin immunoliposomes, nonspecific antibody immunoliposomes, and liposomes containing no antibody. Control cardiomyocytes were incubated in regular medium without any liposomes or antibodies, and another set of controls was kept under normoxic culture conditions. After 24 hours of incubation at 37° C., myocyte survival/viability was assessed as a percentage of the total number of cells in each culture flask by trypan blue exclusion (FIG. 2) or $^3$H-thymidine uptake (FIG. 3). To demonstrate sealing of injured myocytes with liposomes, fluorescein-labeled phospholipids were used in the production of various liposome preparations such as immunoliposomes and liposomes without antibody.

Liposome adherence to cardiomyocytes was assessed by fluorescence and confocal microscopy; electron dense immunoliposomes and liposomes were also prepared for ultrastructural characterization of the treated hypoxic cardiomyocytes by the following protocol:

Two million H9C2 myocytes were cultured in 25 ml culture flasks with DMEM and fetal calf serum at 37° C. in a humidified incubator with 5% $CO_2$ concentration. After the cells were stabilized at 37° C. incubation overnight, the cells were washed with phosphate buffer (pH 7.4) followed by addition of 3 ml fresh medium with or without liposomes (immuno or non-immuno) or antibody. To produce mild hypoxic injury, highly purified nitrogen was bubbled through the medium for 4 minutes without dislodging the cells from the flask bottom, the flasks were closed tightly, and incubated overnight at 37° C. for 24 hours. To induce severe injury, the stream of nitrogen was directed to dislodge almost all the cells from the bottom surface of the culture wells.

Figure 2:
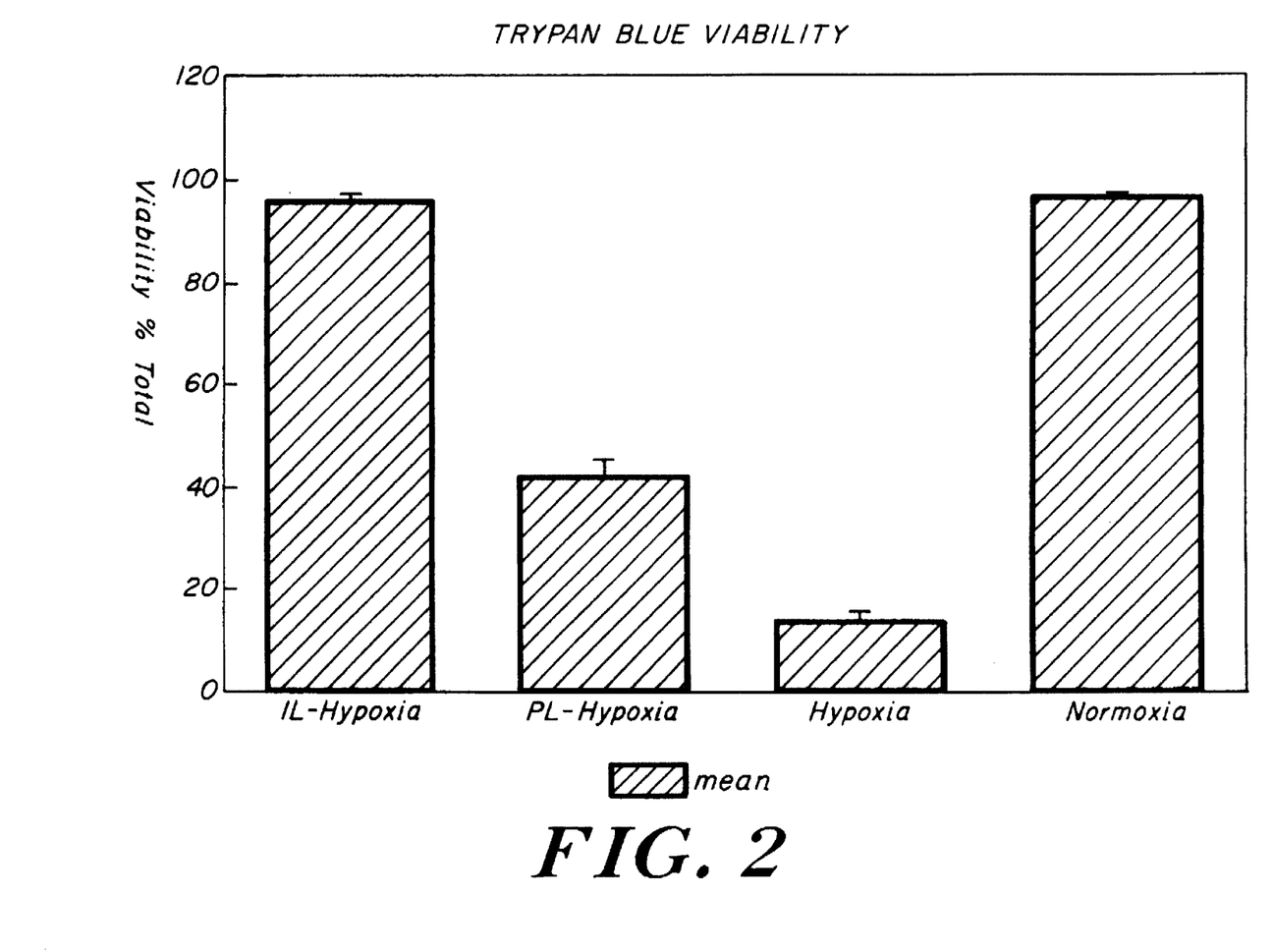
FIG. 2 shows cardiac myocyte H9C2 viability as assessed by a trypan blue exclusion test according to a method of the invention.
Figure 3:
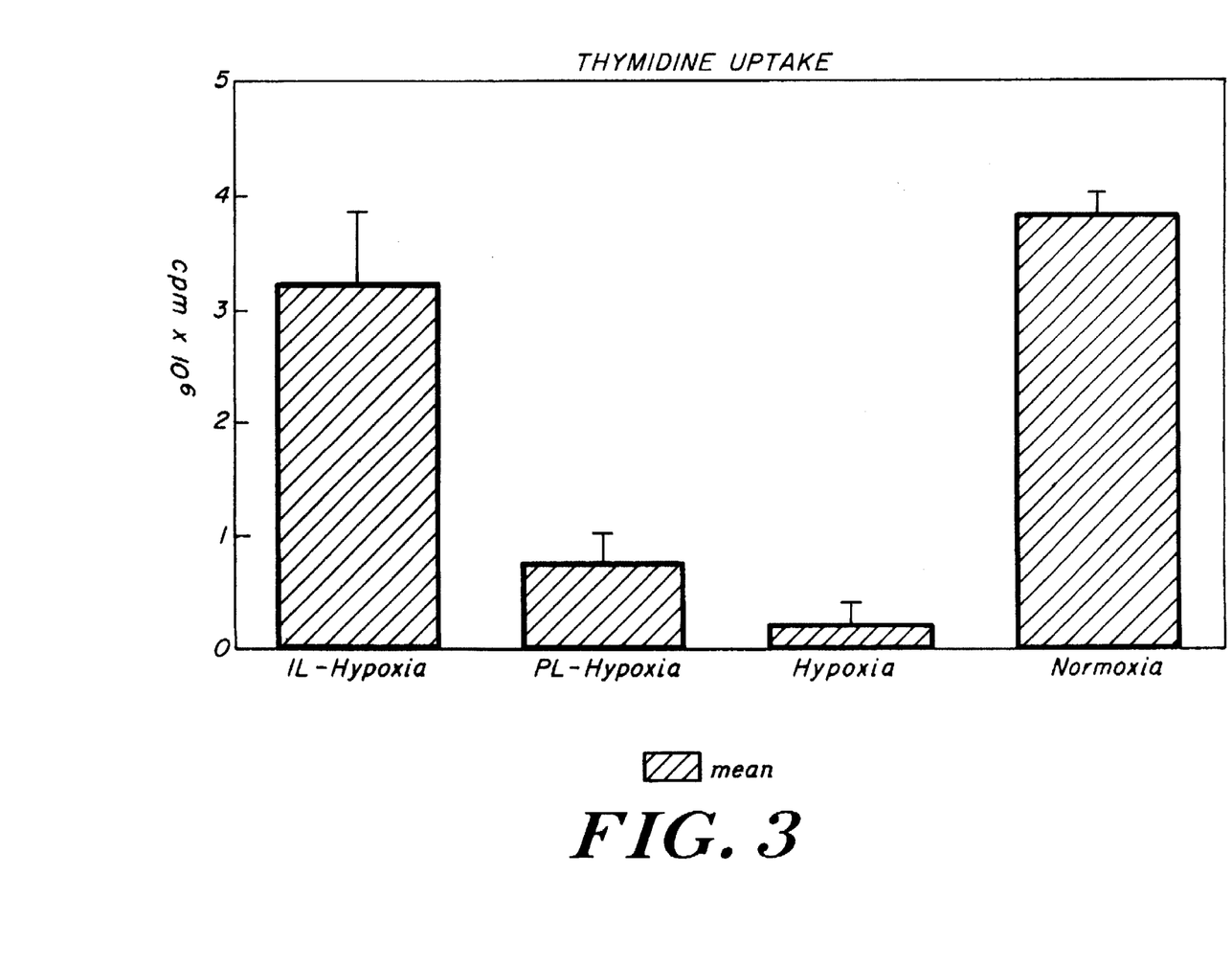
FIG. 3 shows cardiac myocyte H9C2 viability as assessed by $^3$H-thymidine uptake according to a method of the invention.

After an overnight hypoxic injury, only 14% of control myocytes were assessed to be viable by trypan blue exclusion criteria (FIG. 2). Most of the dead cells were recovered in the supernatant. The results showed that liposomes without antibody (42.3%) and nonspecific immunoliposomes provided some protection to the cells from hypoxic injury. This suggested that liposomes, which are a lipid bilayer, can nonspecifically stick to cell surfaces and fortuitously seal some of the cell membrane branches. However, in contrast to the moderate protection provided by liposomes without antibody and nonspecific immunoliposomes, immunoliposomes that were prepared according to the invention to specifically target myosin resulted in extraordinary salvage of the damaged cells from death. These immunoliposomes almost completely prevented cell death (96.2% viability as shown in FIG. 2) relative to 98% of normally grown cells. These results demonstrate that immunoliposome targeting of intracellular antigen produces selective targeting of the areas of myosin exposure and effectively seals the sites of membrane disruption. These severely hypoxic cells also showed cell viability when treated with immunoliposomes as determined by $^3$H-thymidine uptake (FIG. 3). Immunoliposome treated cells had 83–85% viability relative to normoxic controls (100%). In contrast, cells treated with liposomes without antibody had only 19.4% viability, and control hypoxic cells had only 5.2% viability, as assessed by $^3$H-thymidine uptake.

After severe hypoxia injury, myocytes treated with fluorescent immunoliposomes showed re-attachment of myocytes to the culture flasks, indicating cell viability and no loss of myocytes. Normally shaped mycocytes were usually seen as confluent, firmly adherent cultures with fluorescence visible on most of the cells. On the other hand, cultured myocytes treated with liposomes without antibody only demonstrated scattered cells in the culture flasks with fluorescence, or few clusters of cells with fluorescence. Most of these cells did not maintain normal cell morphology and shape, and did not appear healthy. The presence of immunoliposomes on the cell surfaces with retention of cell morphology was confirmed by confocal microscopy. The intensity of fluorescence or distribution of the immunoliposomes varied from myocyte to myocyte and depended on the severity of damage to the cells.

Figure 4A:
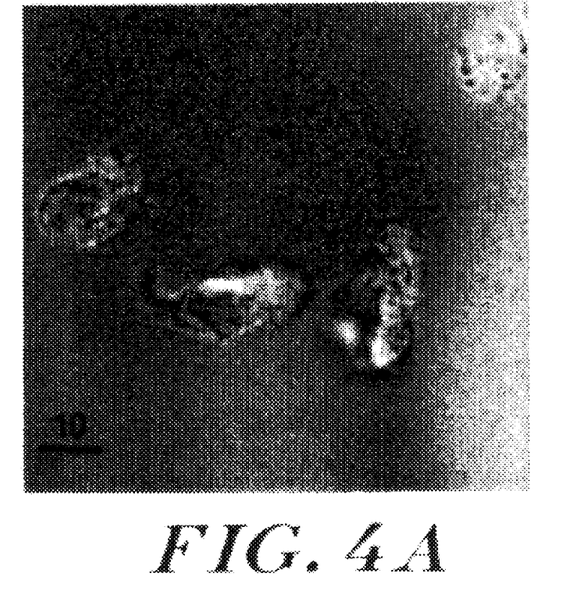
FIG. 4 shows liposome adherence to cardiomyocytes according to a method of the invention as assessed by fluorescence/confocal microscopy.
Figure 4B:
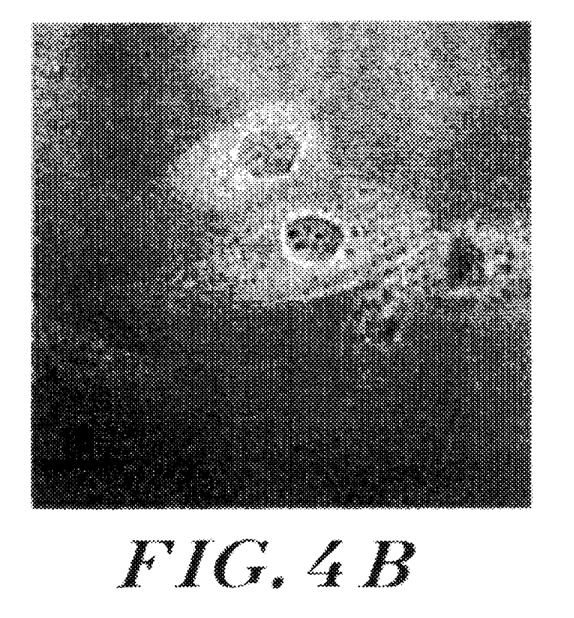

Referring to FIG. 4, the H9C2 rat cardiomyocytes were cultured in hypoxia for 24 hours with either fluorescent liposomes without antibody (left panel) or fluorescent antimyosin immunoliposomes (right panel). The immunoliposomes can be seen anchored (green colored dots) to the hypoxia myocytes (seen as grey background) at the sites of myosin exposure through cell membrane breaches. The myocytes incubated with immunoliposomes were adherently attached to the bottoms of the flask, representing almost complete viability. In contrast, most of the myocytes cultured with plain liposomes in hypoxia conditions were dead and were recovered from the supernatant. The left panel demonstrates some ghost myocytes which are covered with some nonspecific plain liposomes (green hue). The results of this experiment clearly show that if a liposome is directed specifically against an intracellular cytoskeletal protein, it will seek the areas of cell membrane rupture precisely, will plug the breaches and will prevent loss of cell viability.

Figure 5A:
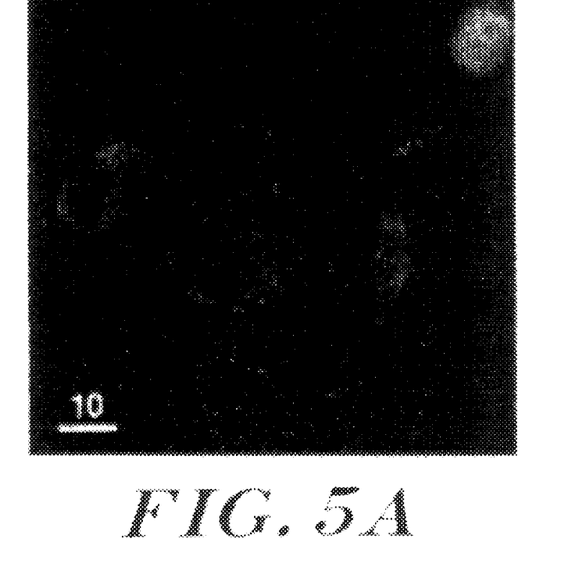
FIG. 5 shows liposome adherence to cardiomyocytes according to a method of the invention as assessed by fluorescence/confocal microscopy.
Figure 5B:
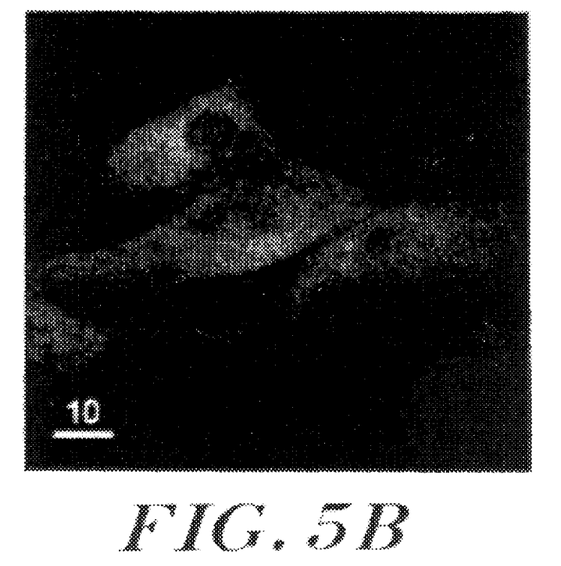

Referring to FIG. 5, liposomes were pseudocolored to enhance visualization of localization of immunoliposomes and liposomes without antibody. The attachment of immunoliposomes to hypoxic myocytes can be delineated. Liposomes without antibody, in the left panel, showed some nonspecific uptake on amorphic nonviable cells.

Figure 6A:
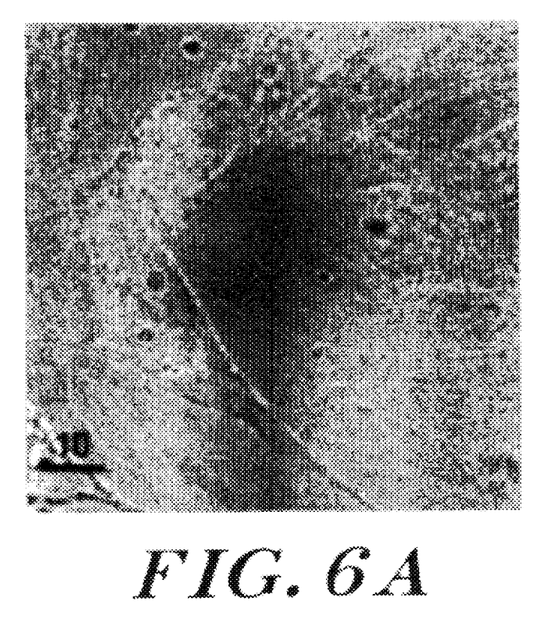
FIG. 6 shows liposome adherence to cardiomyocytes according to a method of the invention as assessed by fluorescence/confocal microscopy.
Figure 6B:
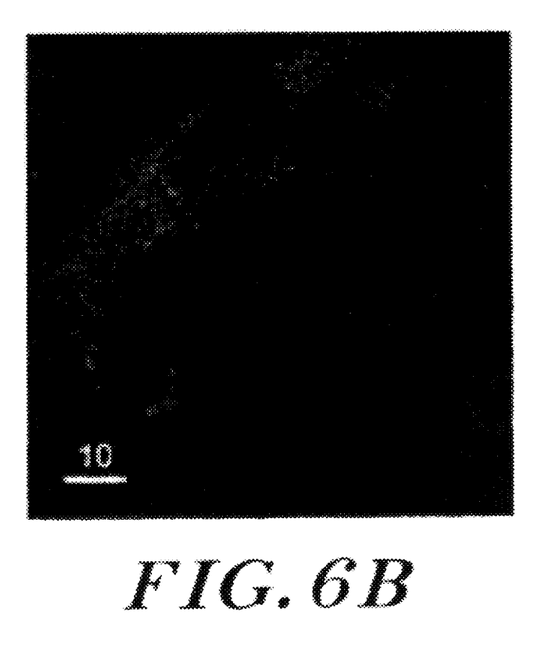

As shown in FIG. 6, another set of H9C2 cardiomyocytes incubated with antimyosin immunoliposomes demonstrated the same protective phenomenon. The left panel demonstrates the superimposition of the green fluorescence of immunoliposomes over the grey cardiomyocytes. The liposome distribution clearly demonstrates the areas of the cardiomyocytes that are normal and did not attract liposomes compared to the areas in the same cell that have dense localization of immunoliposomes. The differential liposomal distribution can be clearly visualized by pseudocolorization (right panel) of the same field of view. The experiment demonstrates the selectivity and specificity of the immunoliposomal localization since the injured areas (with anticipated myosin exposure) attracted the immunoliposomes and the normal areas with intact sarcolemma (and hence unexposed myosin) did not show any localization.

Figure 7A:
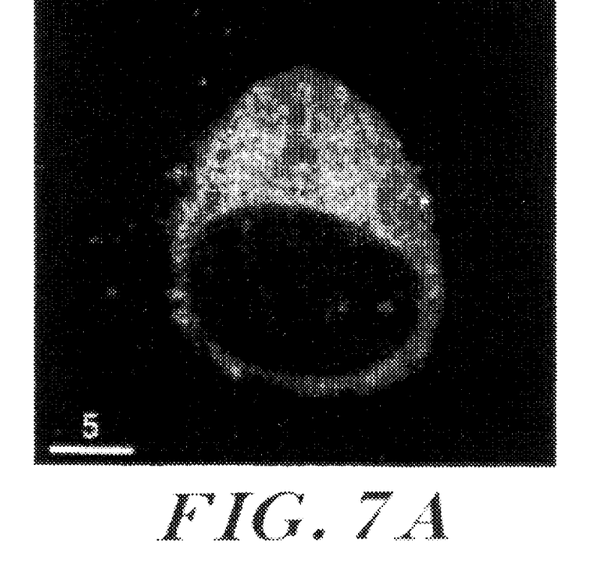
FIG. 7 shows liposome adherence to cardiomyocytes according to a method of the invention as assessed by fluorescence/confocal microscopy.
Figure 7B:
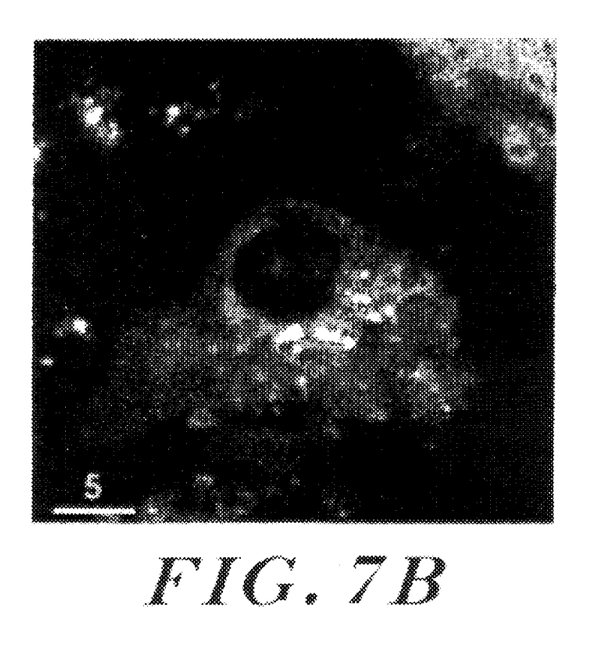

FIG. 7 shows another set of hypoxia H9C2 myocytes incubated with antimyosin liposomes for 5 days. As seen in the pseudocolored micrographs, immunoliposome treated cells were still viable at 5 days when cultured under hypoxia. Although the cell shapes have changed somewhat, the cell membrane is still clearly intact. The fluorescent lipids at this time were observed perinuclearly, appearing to be within the cytoplasm by confocal microscopy. No viable myocytes treated with liposomes without antibody were seen after 5 days.

Figure 8:
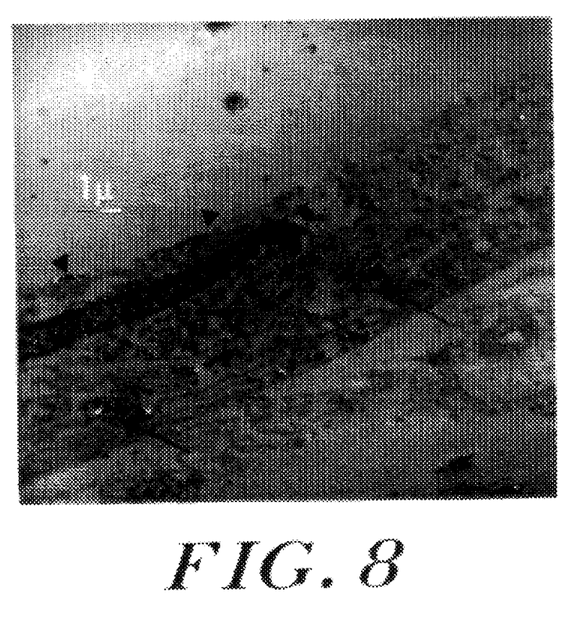
FIG. 8 shows ultrastructure examination of the localization of silver grains containing immunoliposomes according to a method of the invention.

Transmission electron microscopy demonstrated that fusion of the immunoliposomes had occurred with the membrane by demonstrating the attachment of immunoliposomes on the cell membranes as well as by showing intracellular delivery of patchy electron dense intraliposomal contents to otherwise unstained myocytes. Referring to FIG. 8, ultrastructural examination of the localization of silver grains containing immunoliposomes in hypoxia myocytes is shown. Confirmation of intracellular delivery of intraliposomal contents is evident in this electron micrograph. Antimyosin immunoliposomes used for this experiment contained silver grains in the liposomal core. After 24 hours of incubation with hypoxia cardiomyocytes, silver grains (dark black dots) were seen to be associated either with the membrane (arrow heads) above the myofilaments or observed towards the central part of the intracellular space (thin arrows). This experiment utilized silver grains as a model drug/genetic vector for the assessment of targeted intracellular delivery. The extent of silver grains delivered into this cell visible in this thin section suggests that immunoliposomes directed against a cytoskeletal protein may offer a highly efficient tool for gene delivery into cells. The methodology will have an additional advantage of salvaging the stressed cells by plugging the cell membrane breaches.

In vivo Determination of Efficacy of Immunoliposome Sealing

In order to test for immunoliposome efficacy in vivo, e.g., in reduction of myocardial necrosis, a canine myocardial infarct model is used, as described in Khaw et al., Circulation 60:1527 (1979) and Narula et al., Jour. Nuclear Med. 35:1076 (1994), both of which are hereby incorporated by reference. Antimyosin imaging, histochemical and pathological assessment of the infarct sized is performed to compare the efficacy of treatment to reduce infarct size.

1. Canine Model

Mongrel dogs of both sexes weighing 20 to 30 kg are anesthetized with intravenous sodium pentobarbital (30 mg/kg) and ventilated with a Harvard positive-pressure respirator (Harvard Apparatus, South Natick, Mass.). The right femoral artery and vein are isolated and catheterized to facilitate monitoring of arterial pressures and the administration of medication. Arterial pressure and a multilead electrocardiogram are continuously monitored. A left thoracotomy is performed, and the heart is suspended in the pericardial cradle. Proximal and midportions of left anterior descending coronary artery (LAD) are isolated, and a surgical monofilament snare enclosed in polyethylene tubing is placed immediately distal to the first diagonal branch. A small branch just distal to the site of occlusion is cannulated with a 22-gauge catheter for the administration of antimyosin immunoliposomes into the LAD. The LAD is occluded by tightening the snare, and a prophylactic lidocaine infusion of 0.1 mg/kg is maintained for 1 hour. At 1.5 hour, the LAD territory is reperfused by removal of the snare. At the time of reperfusion, approximately one-half the animals are randomly selected to receive a single dose of immunoliposomes dissolved in 10 ml of 0.9 percent saline through the LAD cannula at a rate of 1.1 ml/min. The remaining animals receive the same volume of intracoronary saline. The animals are killed at 24 hours or 7 days later by atrial injection of 20 to 40 mEq of potassium chloride for histolochemical and histological characterization of the infarcted myocardium. The heart is excised, the atria are removed, the ventricular mass is recorded in grams, and the ventricle is sliced into 1 cm thick slices.

Cell membrane sealing is assessed by survival/viability testing of tissue, using nitroblue tetrazolium staining. Alternatively, to demonstrate liposome sealing of injured cells, fluorescein-labeled phospholipids are used in the preparation of immunoliposomes, and detection of liposome adherence to cardiomyocytes is assessed by fluorescence microscopy and confocal microscopy, as taught herein. Light microscopy followed by transmission electromicroscopy are other methods of assessment of cell viability. Functional assessment of the hearts in vivo can be performed using gated blood pool imaging or echocardiography. Immunoliposome treated and saline treated animals will be compared.

2. Antimyosin Antibodies

A monoclonal antimyosin antibody was generated by hybridization of immune murine spleen cells with SP2/OA murine myeloma cells, purified by methods previously described (Khaw et al., Hybridoma 3:11–23, 1984, hereby incorporated by reference), and numbered 2G42D7 (as referred to herein). The bicyclic anhydride of diethylenetriamine pentaacetic acid (DTPA) is prepared by the method of Hnatowich et al. (Hnatowich et al., Science 220:613–615, 1983, hereby incorporated by reference) for coupling with antimyosin-Fab. The molar ratio of DTPA to Fab was 1:1. Two approaches may be used to label antimyosin Fab, $^{111}$In coupling to the DTPA and $^{123}$I coupling directly to the protein using chloramine-T.

Indium Labeling.

Approximately 37 MBq (1 mCi) of $^{111}$InCl is used to label 100 μg of DTPA-R11D10-Fab. To a 1-mCi aliquot (50 μl) of $^{111}$InCl, an equal volume of 1M sodium citrate (pH 5.5) is added, followed by an aliquot of antimyosin-Fab. The reaction mixture is allowed to incubate at room temperature for 30 min. Antibody-bound $^{111}$In is separated from free $^{111}$In by SEPHADEX (Sigma Chemical, St. Louis, Mo.) G-25 column (10 ml) chromatography. The peak tubes in the void volume containing the radiolabled antibody are pooled and used within 1 hour of radiolabeling. An average of 80% of the initial antibody concentration is recovered in the peak tubes containing the radiolabeled antibody.

Iodination.

Radioiodination is accomplished by the chloramine-T method, as described by Hunter and Greenwood (Hunter et al., Nature 194:495–496, 1962) to label antimyosin Fab with $^{123}$I. To a 100 μg aliquot of DTPA-coupled antimyosin Fab antibody in 0.1M phosphate buffer (pH 7.4), 37 MBq (1 mCi) of $^{123}$I is added and mixed thoroughly. A 10-μl aliquot of chloramine-T (26 mg/ml in 0.5M phosphate buffer, pH 7.4) is added followed by mixing for 2 min. Iodination is terminated by the addition of 25 μl of 0.1M methionine plus 0.1M cresol. The reaction mixture is then applied to a 10-ml SEPHADEX G-25 column to separate free and protein-bound radioiodine.

Antimyosin Antibody Imaging.

The following sets of images are recorded in each animal: in vivo during the experiment, of the whole heart ex vivo and as 1-cm ring slices cut perpendicular to the long axis of the left ventricle. Scintigraphic images are obtained using a gamma camera (Ohio-Nuclear 100, Solon, Ohio) equipped with a medium-energy collimator. The pulse height analyzer are set at center lines of 247 and 159 keV with 20% windows for $^{111}$In and $^{123}$I radioisotopes, respectively. Concurrent with antibody injections, sequential 1-min acquisition images are recorded for a total of 8 min. The excised hearts are imaged whole and as 1-cm thick slices for both isotopes. Background images are also collected at each isotope setting for identical acquisition time. The background corrected and peak-normalized sets of images are recorded on floppy disks and the experiment number, treatment and sequence of injection of $^{111}$In-and $^{123}$I-labeled antimyosin antibody are blinded. The infarct size is assessed twice individually by three observers. Semiautomatic planimetry is performed with a Technicare 560 computer (Technicare Corp., Solon, Ohio) to determine the infarct size as the number of pixels, as previously described (Khaw et al., J. Nucl. Med. 28:76–82, 1987). The pixel size is calibrated, and the absolute volume of infarcted tissue is determined (area×slice thickness). This value, multiplied by the specific gravity of myocardium (1.05), is used to determine the weight of the infarcted tissue in grams (Ostrzega et al., Am. Heart J. 117:444–452, 1989). The percent infarct relative to the ventricular mass is then calculated for the statistical analysis.

Targeted Delivery of DNA

Several methods have been used for the delivery of DNA into cells, including poly-L-lysine conjugated lipids (Zhou et al., Biochim. Biophys. Acta. 1065:8–14, 1991), pH sensitive immunoliposomes (Gregoriadis, G., Liposome Technology, Vol I, II, III, CRC, 1993), and cationic liposomes (Felgner et al., Proc. Natl. Acad. Sci., USA, 84:7413–7417, 1987). However, the drawback with all of these methods is the insufficient uptake and expression of selected genes (DNA). Gene delivery and transfection can be enhanced by the use of hypoxic injury and immunoliposomes as targeting modality. Transmission electron micrographs showed that immunoliposomes can be used to deliver hundreds or more units of intraliposomal contents into an individual target cell (FIG. 8).

Dosage and Mode of Administration

Immunoliposomes administered according to the invention are administered intravenously, intraperitoneally or directly to the target tissue or organ, at a dosage that is appropriate for the amount of biological agent or genetic material that is encapsulated by the liposome. Immunoliposome dosage will therefore vary from about 5 mg/kg body weight to about 1 gm/kg body weight, and may be in the range of 100 mg–500 mg/kg body weight.

OTHER EMBODIMENTS

Other embodiments will be evident to those of skill in the art. It should be understood that the foregoing detailed description is provided for clarity only and is merely exemplary. The spirit and scope of the present invention are not limited thereto, being defined by the claims set forth below.

What is claimed is:

1. A method of inhibiting cell death in cardiac tissue, said method comprising providing cardiac tissue comprising injured cardiomyocytes having intracellular myosin exposed to the exterior of said cardiomyocytes;

contacting said injured cardiomyocytes with a specific affinity reagent-liposome conjugate, said specific affinity reagent comprising an antibody specific for said intracellular myosin, for a time sufficient to allow said conjugate to adhere to said intracellular myosin; and determining the viability of said cardiomyocytes.

2. The method of claim 1, wherein said conjugate comprises a biological agent.

3. The method of claim 2, wherein said biological agent is selected from the group consisting of fibroblastic growth factor-β, angiogenic factors, high energy substrates for the myocardium, antioxidants, cytokines and contrast agents.

* * * * *